United States Patent
Fujimura et al.

(10) Patent No.: US 7,439,073 B2
(45) Date of Patent: Oct. 21, 2008

(54) KIT FOR BIOCHEMICAL SENSOR AND MEASURING APPARATUS

(75) Inventors: Toru Fujimura, Asaka (JP); Juergen Pipper, Jena (DE)

(73) Assignee: Hitachi, Ltd., Tokyo (JP)

( * ) Notice: Subject to any disclaimer, the term of this patent is extended or adjusted under 35 U.S.C. 154(b) by 640 days.

(21) Appl. No.: 10/372,288

(22) Filed: Feb. 25, 2003

(65) Prior Publication Data
US 2004/0070764 A1    Apr. 15, 2004

(30) Foreign Application Priority Data
Oct. 10, 2002    (JP)    ............................ P2002-296870

(51) Int. Cl.
G01N 21/00    (2006.01)
G01N 33/543    (2006.01)
G01N 1/10    (2006.01)
C12Q 1/70    (2006.01)
G01B 11/02    (2006.01)

(52) U.S. Cl. ........................... 436/164; 436/518; 435/5; 356/504; 356/246

(58) Field of Classification Search ................ 436/164, 436/518; 356/504, 246; 435/5
See application file for complete search history.

(56) References Cited

U.S. PATENT DOCUMENTS

| | | | | |
|---|---|---|---|---|
| 4,192,056 A | * | 3/1980 | Logan et al. ................... | 29/468 |
| 5,418,136 A | * | 5/1995 | Miller et al. ................... | 435/5 |
| 5,468,606 A | * | 11/1995 | Bogart et al. .................. | 435/5 |
| 5,512,492 A | * | 4/1996 | Herron et al. ................. | 436/518 |
| 6,248,539 B1 | * | 6/2001 | Ghadiri et al. ................ | 435/7.1 |
| 6,537,829 B1 | * | 3/2003 | Zarling et al. ................ | 436/514 |
| 6,933,112 B1 | * | 8/2005 | Drewes et al. ................. | 435/6 |
| 7,070,987 B2 | * | 7/2006 | Cunningham et al. .... | 435/287.1 |

(Continued)

FOREIGN PATENT DOCUMENTS

DE    42 00 088 A1    1/1992

(Continued)

OTHER PUBLICATIONS

Jenison et al., Interference-based detection of nucleic acid targets on optically coated silicon, Jan. 2001, Nature Biotechnology, vol. 19, pp. 62-65.*

(Continued)

*Primary Examiner*—Jill Warden
*Assistant Examiner*—Lore Ramillano
(74) *Attorney, Agent, or Firm*—Reed Smith LLP; Stanley P. Fisher, Esq.; Juan Carlos A. Marquez, Esq.

(57) ABSTRACT

An object of the present invention is to provide a simple biochemical sensor making use of the light interference effect of an optical film which is capable of measuring binding of biochemical substances at a high throughput. In the present invention, a solution containing samples 18 is passed through the sensor having probes 17 provided on an optical film with a refractive index of not less than 1.8 and not greater than 3 on a substrate, and binding of the probes 17 and samples 18 is detected from the change of intensity of the reflected light. This makes it possible to measure binding of biochemical substances at a high throughput with high precision.

4 Claims, 16 Drawing Sheets

U.S. PATENT DOCUMENTS

2001/0040680 A1* 11/2001 Kubo et al. .................. 356/445
2002/0042070 A1* 4/2002 Saraf et al. ..................... 435/6

FOREIGN PATENT DOCUMENTS

| JP | 63-078051 | 9/1986 |
| JP | 63-078052 | 9/1986 |
| WO | WO 02/061429 A2 | 8/2002 |

OTHER PUBLICATIONS

Torbjorn Sandstrom, Manne Stenberg and Hakan Nygren, "Visual Detection of Organic Monomolecular Films by Interference Colors", Applied Optics, vol. 24, No. 4 (Feb. 15, 1985) pp. 472-479.

M. Inoue, K. Ohtaka and S. Yanagawa, "Light Scattering from Macroscopic Spherical Bodies. II Reflectivity of Light and Electromagnetic Localized State in a Periodic Monolayer of Dielectric Spheres", Physical Review B, vol. 25, No. 2 (Jan. 15, 1982) pp. 689-699.

* cited by examiner

INTERFERENCE COLOR IS HARDLY OBTAINABLE IN VISIBLE LIGHT REGION WHEN FILM THICKNESS IS LESS THAN 20 nm

FIG. 13
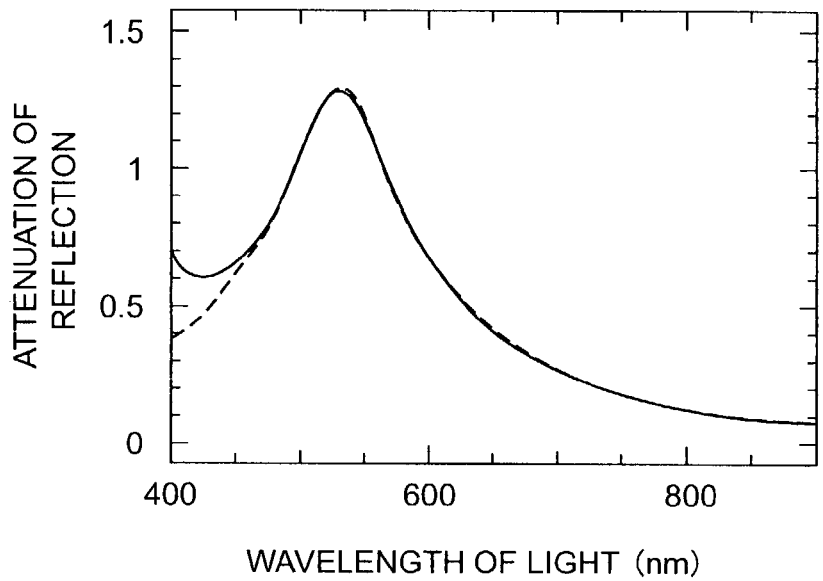
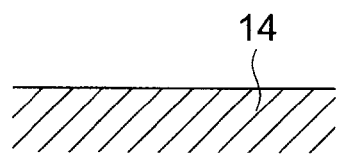
FIG. 14A
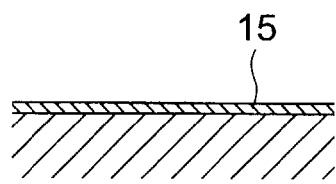
FIG. 14B
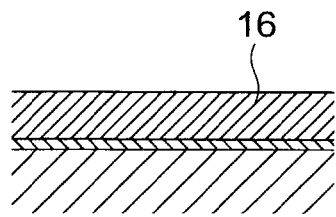
FIG. 14C

IN THE REGION WHERE REFRACTIVE INDEX IS LESS THAN 1.8, DETECTION IS VERY DIFFICULT BECAUSE OF SMALL DIFFERENCE IN REFRACTIVE INDEX BETWEEN TRANSPARENT LAYER AND AQUEOUS SOLUTION

US 7,439,073 B2

KIT FOR BIOCHEMICAL SENSOR AND MEASURING APPARATUS

BACKGROUND OF THE INVENTION

The present invention relates to a biochemical sensor making use of an optical film, component members of such a sensor, and a measuring apparatus using the same.

Hitherto, labeling of radioactive or fluorescent substances has been resorted to for the measurement of binding of biochemical substances such as antigen-antibody reactions. This labeling, however, was time-consuming, and especially labeling of proteins was complex in its process and could cause a change of properties of the labeled protein.

A biochemical sensor making use of a change of interference color of an optical film is known as a means for the direct measurement of binding between biochemical substances with ease without resorting to labeling. Such a biochemical sensor is described in a paper by Sandestrom et al (Appl. Opt., 24, 472, 1985). An example thereof is here explained by referring to FIG. 1. A thin optical film 2 is provided on a substrate 1. Refractive index of the air is 1.00, so the optical film 2 is made of a material with a refractive index of 1.50 while the substrate 1 is made of a material whose refractive index is 2.25. When the optical film is designed to have a thickness which, in terms of optical length, is ¼ of wavelength $\lambda_0$ of visible light or odd multiples thereof (such as $3/4\lambda_0$ or $5/4\lambda_0$), the optical film functions as an antireflection film, and as shown in FIG. 2, intensity of the reflected light in the direction perpendicular to the optical film becomes 0 at wavelength $\lambda_0$ as in the reflection spectrum A of FIG. 2. Consequently, the sensor produces an interference color. A monomolecular layer of the first biochemical substance 3 is provided on said optical film 2. In case the biochemical substance is protein, refractive index of the layer is about 1.5 and its thickness is around 10 nm. This optically represents an increase of thickness of the optical film, and the reflection spectrum changes from the solid line A to the dotted line A' in FIG. 2, producing a corresponding change of interference color. When this first biochemical substance 3 is biochemically bound with a second biochemical substance 4, a further increase of film thickness is induced, providing a change from the dotted line A' to the broken line A" in FIG. 2 and a corresponding change of interference color. Thereby binding of the second biochemical substance is detected. In the ordinary procedure of detection, there is initially prepared a sample comprising a monomolecular layer 3 of a first biochemical substance covering optical film 2 on substrate 1. This sample is put into a solution of a second biochemical substance, then taken out from the solution and dried, after which the change of interference color from the dotted line A' to the broken line A" in FIG. 2 is examined. Thus, in the prior art, the sensor is taken out into the air and dried, and then interference color is determined.

According to the sensor described in the above paper, however, since the sensor is once taken out into the air and dried before determining interference color, time is taken for the drying step and a high throughput is hardly obtainable.

Further, since measurement is conducted after the passage of a predetermined period of time from start of the reaction, the sensor might be taken out into the air before the reaction is saturated, depending on the way of setting of the predetermined period of time, so that the measurement is not always accurate. On the other hand, when the predetermined period of time is set long to make sure that the measurement is made after the reaction has been sufficiently saturated, time efficiency is bad since the sensor is left immersed in the solution even after the reaction has been saturated.

SUMMARY OF THE INVENTION

The present invention is intended to provide a simple biochemical sensor making use of the light interference effect of optical film and capable of measuring binding of biochemical substances at a high throughput.

The above object of the present invention can be implemented by the following conception.

(1) To a sensor chip comprising a thin optical film formed on a substrate and probes formed on the optical film surface, a solution containing a sample which interacts with said probes is supplied, and in a state where this solution has been supplied, the intensity of reflected light which varies between before and after the interaction is detected. The optical film is made of a material which differs greatly in refractive index from the aqueous solution containing the sample, namely a material whose refractive index is not less than 1.8, such as titanium oxide, zirconium oxide, hafnium oxide and tantalum oxide. Use of an optical film having a refractive index differing greatly from that of the aqueous solution makes it possible to determine, even in water, the change of reflected light intensity caused by interference of light before and after the reaction between the probe and the sample. Refractive index of the optical film material is preferably not greater than 3.0. This is because the refractive index of said materials is not greater than 3.0, and also because the higher the refractive index of optical film is, the smaller the change of interference color by binding of biochemical substances becomes. Also, thickness of this transparent layer should be not less than 10 nm but not greater than 10 μm for the reason that if the layer thickness is less than 10 nm, it is hard to obtain interference color in the visible light region, while if the thickness is greater than 10 μm, the structure of light interference appearing on the reflection spectrum is too fine and impractical for the sensor of the present application.

In the present invention, binding between the biochemical substances is detected principally by making use of the change of interference color of optical film in a solution. Here, the term "biochemical substances" is used to refer to the substances which can be bound biochemically with other substances, which include not only the materials produced in vivo, such as proteins, nucleic acids, lipid and saccharides, but also exogenous materials bound with the in vivo particles, such as medicinal substances and endocrine disruptors.

The above-mentioned biochemical sensor was designed to be used for the measurement in the atmospheric air. In such measurement in the atmospheric air, as mentioned in the paper by Sandstrom et al (Appl. Opt., 24, 472, 1985), it has been believed that an optical film with refractive index of not less than 1.5 was suited for the sensor. On the other hand, the "solution containing the sample" is an aqueous solution containing biochemical substances. Refractive index of this aqueous solution, although variable depending on the concentration of biochemical substances, is approximately 1.3330 which is the refractive index of pure water. In a solution, the background refractive index becomes higher by more than 0.3 than the refractive index 1.0 of the atmospheric air, so that when using an optical film with refractive index of around 1.5 as in the prior art, the light reflectance caused by the difference in refractive index between background and optical film becomes small. In the present invention, in contrast, the optical film is designed to have a refractive index of not less than 1.8, which is greatly different (greater by more than 0.467) from the refractive index 1.3330 of pure water, so that it is possible to detect the reaction sufficiently before the sensor is dried. Detection of the reaction is further facilitated by selecting the substrate or the reflective layer thereon so that distinct interference color will appear when background refractive index is 1.3330.

(2) A thin optical film having openings is provided on the substrate. The inner wall of each opening is modified for fixating a probe. In practicing actual detection, a sample containing a biochemical substance which interacts with the probe is flown through the kit having provided on the substrate an optical film having openings where the probes are fixated, and the interaction is detected by using light.

Other objects, features and advantages of the invention will become apparent from the following description of the embodiments of the invention taken in conjunction with the accompanying drawings.

BRIEF DESCRIPTION OF THE DRAWINGS

FIG. 13 is a graphic approximation of the reflection spectrum before protein binding.

FIGS. 14A, 14B and 14C are flow sheets for producing the biochemical sensor of the present invention.

DESCRIPTION OF REFERENCE NUMERALS

1: substrate, 2: optical film, 3: first biochemical substance, 4: second biochemical substance, 5: substrate, 6: reflective layer, 7: optical film, 8: reflective layer, 9: first biochemical substance, 10: opening, 11: first biochemical substance, 12: silica beads, 13: sensor section.

DETAILED DESCRIPTION OF THE INVENTION

In the present invention, since the space in the opening provides the region for sensor operation, the area of sensor operation is widened as compared with the flat films, making it possible to obtain a greater change of interference color by binding of many biochemical substances.

The size (diameter) a of the opening is preferably not less than 10 nm for taking in proteins. Also, the distance between the adjoining openings is made less than the wavelength of light so that the structure in the direction parallel to the film won't work as diffraction grating, allowing simplification of the spectrum. Thus, the distance between the adjoining openings is preferably selected to be less than the wavelength of light used for the detection. It is to be further noted that the smaller the size b of the convex portion (interval between the openings), the larger the increase of effective optical path length by binding of the biochemical substances. In view of the above, the size a of the opening is preferably 100 to 400 nm and the size b of the convexity is preferably 50 to 350 nm in the case of the sensor in which detection is made in the visible light region. The openings may not necessarily be columnar; for instance, the convex portion may be designed to be columnar with a diameter b and the aperture may be formed as a stripe-like groove with a width a.

Thus, the structure having openings in the optical film can of course be applied where refractive index of the optical film differs greatly from that of the aqueous solution, but this structure is also applicable in case where the optical film is made of a material with a refractive index on the order of 1.4 to 1.6, which is relatively close to the refractive index of background water, such as $SiO_2$, polystyrene and PMMA.

Even with the structure having openings in the optical film, it is possible to detect the change of interference color in a state where an aqueous solution is being flown since interference color varies greatly between before and after the reaction.

The above phenomenon was confirmed in the manner described below.

Figure 1:
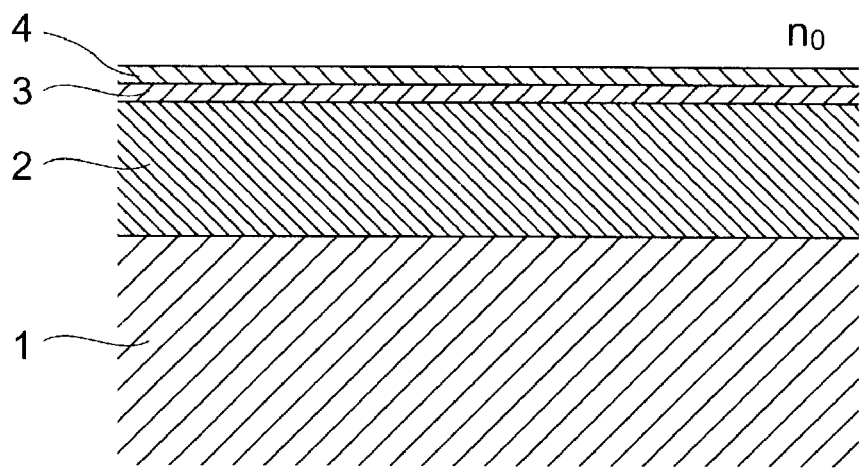
FIG. 1 is a schematic illustration of a conventional biochemical sensor.
Figure 2:
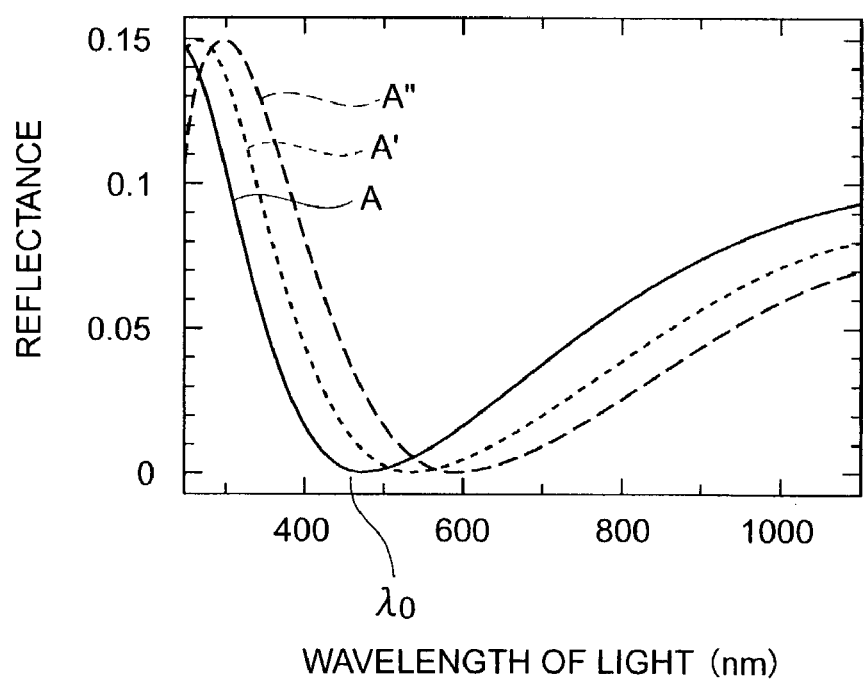
FIG. 2 is a graphic representation of the change of interference color of the conventional biochemical sensor.
Figure 3:
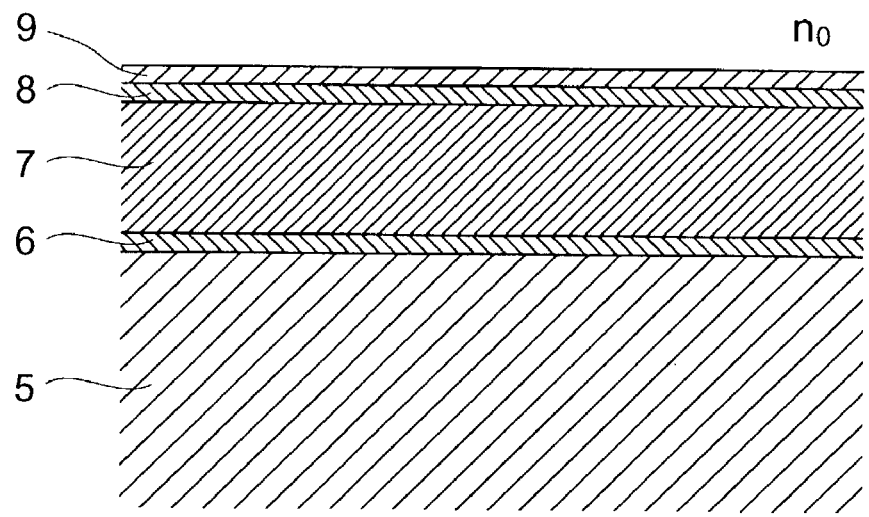
FIG. 3 is a schematic illustration of the principle of the present invention.
Figure 4:
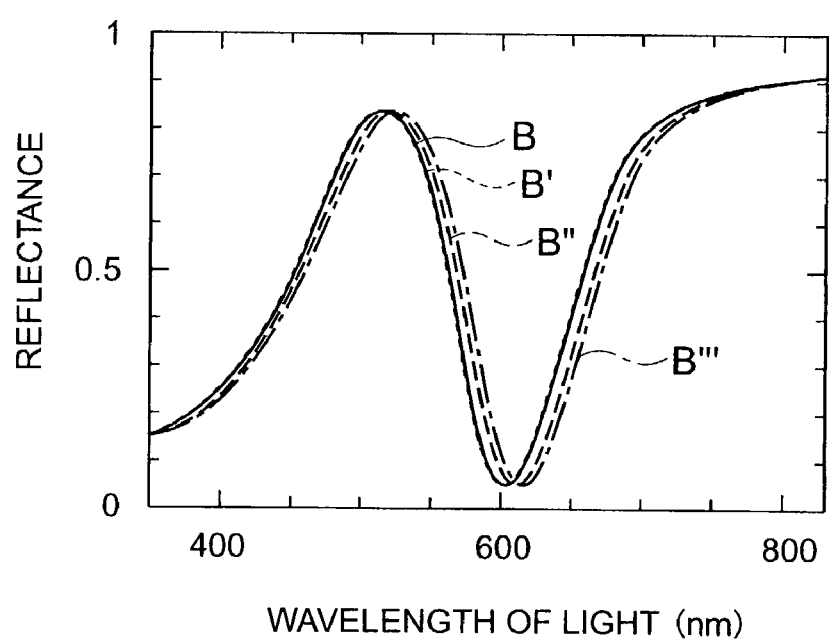
FIG. 4 is a graphic representation of the change of interference color in the present invention.
Figure 5:
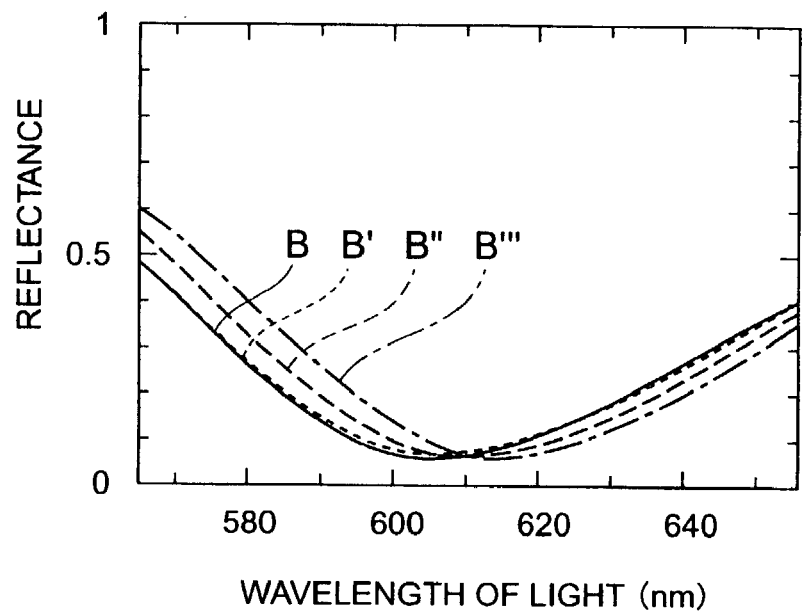
FIG. 5 is also a graphic representation of the change of interference color in the present invention.

Because of detection in a solution, the optical film is so designed that it will develop clear interference color in the solution. With the structure comprising a substrate 1 with a refractive index of 2.25 and an optical film 2 with a refractive index of 1.5 explained above with reference to FIG. 1, there can not be obtained clear interference color since reflection of light between the solution and the optical film is weakened because refractive index of the sensor approximates to refractive index $n_0$ of the solution. Here, as the solution, principally an aqueous solution of a biochemical substance, salt or surfactant is used. Refractive index of pure water is 1.3330, while refractive index of the aqueous solution varies depending on the concentration of the biochemical substance, salt or surfactant and other factors. So, here, in order to intensify reflection of light at the interface between the solution and the optical film, a thin reflective layer is provided on the optical film. No such reflective layer is needed if refractive index differs sufficiently between optical film and aqueous solution. An example of this structure is illustrated in FIG. 3. Substrate 5 is made of glass with a refractive index of 1.5, and a reflective layer 6 is provided thereon. Here, reflective layer 6 is composed of 20 nm thick aluminum deposit. On this reflective layer 6 is provided an optical film 7 made of a transparent material. Reflective layer 6 may be omitted when a light reflective material is used for substrate 5. Here, a transparent material with a refractive index of 1.5 and a thickness of 150 nm was used for optical film 7. On this optical film was further provided a 25 nm thick reflective layer 8 made of gold. In this embodiment, $n_0$ is supposed to be 1.3330 which is the refractive index of pure water. With this structure, as noted from the reflection spectrum shown by solid line B in FIGS. 4 and 5, reflectance is minimized at wavelength 605.5 nm because of attenuation of reflection by the interference effect between reflective layers 6 and 8. FIG. 5 is an enlarged view of the wavelength region of 565 nm to 655 nm on the horizontal axis of the graph of FIG. 4. Hereinafter, the wavelength that provides this minimal reflectance is called reflection attenuation wavelength $\lambda_{AR}$. When calculating the change of interference color when a layer 9 of a first biochemical substance with a refractive index of 1.5 and a thickness of 10 nm was formed on reflective layer 8 as shown in FIG. 3, it is noted that although a change from solid line B to dotted ling B' in FIGS. 4 and 5 is produced, $\lambda_{AR}$ varies only by 0.8 nm. Similarly, when binding of a second biochemical substance to the first biochemical substance 9 is calculated on the supposition that a layer of second biochemical substance with a refractive index of 1.5 and a thickness of 10 nm was formed on the first biochemical substance, $\lambda_{AR}$ changes only by 0.5 nm to the longer wavelength side from B'. This is considered attributable to the small change of interference color incidental to the change of refractive index caused by the incorporation of a biochemical substance layer in addition to the reflective layers 6 and 8, because of the fact that interference color is characterized by light interference effect between said reflective layers 6 and 8.

Figure 6:
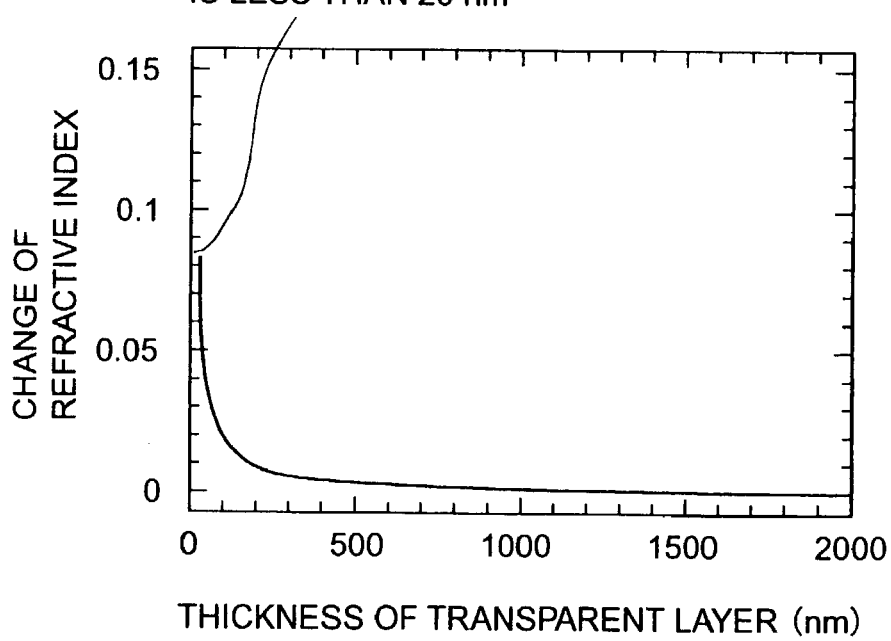
FIG. 6 is a graphic illustration of the principle of the present invention.

In contrast, in case refractive index of the transparent layer of FIG. 3 is changed, $\lambda_{AR}$ changes delicately. The change of refractive index by the layer of the first biochemical substance in FIG. 3 is made from background refractive index of 1.3330 to 1.5 along the thickness of 10 nm. The amount of change $\Delta n$ of refractive index in this operation was 0.167. Refractive index of transparent layer 7 was changed so that the product of $\Delta n$ and thickness will be equalized, that is, so as to provide a same change of optical path length, and the amount of change of $\lambda_{AR}$ was compared. Since the thickness of transparent layer 7 is 150 nm, the reflection spectrum was calculated by increasing the refractive index of transparent layer 7 by 0.011 based on the above condition. Broken line B" in FIGS. 4 and 5 shows the reflection spectrum when refractive index of transparent layer 7 was made 1.511. The amount of change of $\lambda_{AR}$ from solid line B to broken line B" in FIGS. 4 and 5 was approximately sextupled in comparison with the amount of change of $\lambda_{AR}$ from solid line B to dotted line B', providing a shift of 4.7 nm to the longer wavelength side. There was similarly conducted comparison of the amount of change of $\lambda_{AR}$ on binding of the second biochemical substance. When $\lambda_{AR}$ was determined by increasing the refractive index of transparent layer 7 by 0.011 from 1.511, there was seen here again a change from broken line B' to one-dot chain line B''', providing a shift of $\lambda_{AR}$ from B" to 4.7 nm on the longer wavelength side. Thickness of transparent layer 7 for conducting detection by using visible light is between 20 nm and 1.5 μm. This is for the reason that if the layer thickness is less than 20 nm, it is difficult to obtain interference color in the visible region since interference effect appears principally in the ultraviolet region, while if the layer thickness is greater than 1.5 μm, the change of interference color for the amount of binding of the second biochemical substance is lessened. This can be accounted for by the fact that when the thickness of transparent layer 7 is 150 nm, there takes place a change of refractive index of 0.011, but the relation between this change of refractive index and thickness of transparent layer 7 is inversely proportional as shown in FIG. 6, so that the change of refractive index is small, hence the change of interference color is lessened, when the thickness is greater than 1.5 μm. Thus, by making good use of the change of optical path length between the reflective layers, detection of the biochemical substances with higher sensitivity may be realized.

Figure 7:
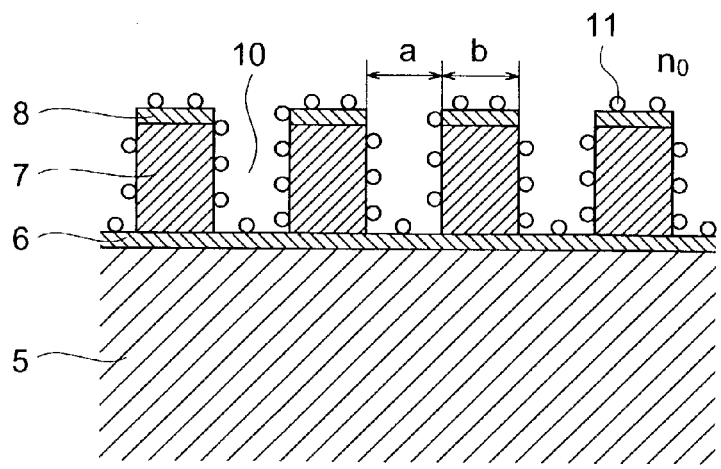
FIG. 7 is a diagrammatic structural illustration of the biochemical sensor of the present invention.
Figure 8A:
FIGS. 8A, 8B, 8C, 8D, 8E, 8F and 8G are flow sheets for producing the biochemical sensor of the present invention.
Figure 8B:
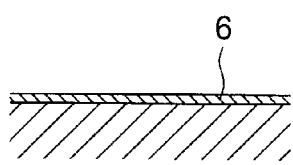
Figure 8C:
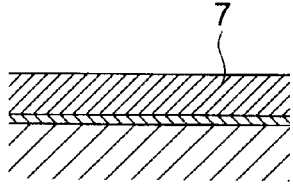
Figure 8D:
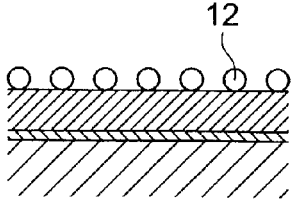
Figure 8E:
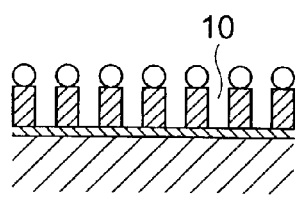
Figure 8F:
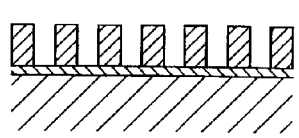
Figure 8G:
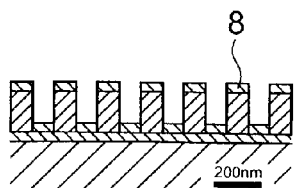

In order to let a solution and a biochemical substance enter the optical film (transparent layer) to change its refractive index, openings 10 for receiving the biochemical substances in the optical film are provided as shown in FIG. 7. Provided with such openings, the optical film has a structure oriented in the direction parallel to the film. Reflection of light from an optical film having such a structure gives rise to a complex light-scattering phenomenon attributable to the structure as discussed in the Theory of Light Scattering of Two-dimensional Regular Arrangement of Dielectric Balls by Inoue and Otaka (Phys. Rev. B, 25, 689, 1982), but in terms of primary approximation, there is produced light interference of the film with an averaged value of refractive index of the structure and refractive index of the aqueous solution, namely light interference is caused by refractive index with an averaged value of refractive index of water and that of the transparent layer having openings. Therefore, refractive index between the reflective layers is increased effectively by binding of a second biochemical substance to the first biochemical substance 11 fixated in openings 10, and this provides a corresponding increase of optical path length. Consequently, $\lambda_{AR}$ is shifted to the longer wavelength side.

(3) Further, the concept of the present invention can be materialized by an optical fiber which applies light to the probes and detects the reflected light, and a detecting device provided with measuring equipment for measuring the change of intensity of the reflected light.

Here, since optical fiber is provided for every type of probe, it is possible to detect the plural different types of reactions almost simultaneously.

DESCRIPTION OF PREFERRED EMBODIMENTS

EXAMPLE 1

Processes for producing a sensor for detecting binding of biochemical substances at high sensitivity are described below. FIG. 14 is a schematic illustration of an example of the sensor producing process. On a flat-surfaced glass substrate 14 with a refractive index of 1.5 is vacuum deposited a 5 nm thick reflective layer of aluminum 15. On this reflective layer is further deposited a 120 nm thick transparent layer of titanium oxide (TiO$_x$, refractive index 2.4) 16, followed by surface treatment with 3-aminopropyltrimethoxysilane to introduce an amino group into the surface of transparent layer 16. 2 mg of N-hydroxysuccinimide, 10 mg of water-soluble carbodiimide and 1 mg of an antibody are dissolved in 1 ml of deionized water to activate the carboxyl group of the antibody. This solution is dropped onto the amino group-introduced portion of the deposit, and the antibody is fixated to the amino group in the sensor surface by covalent bonding. Thereafter, the sensor chip is rinsed with deionized water and dried by blowing nitrogen gas.

Figure 15A:
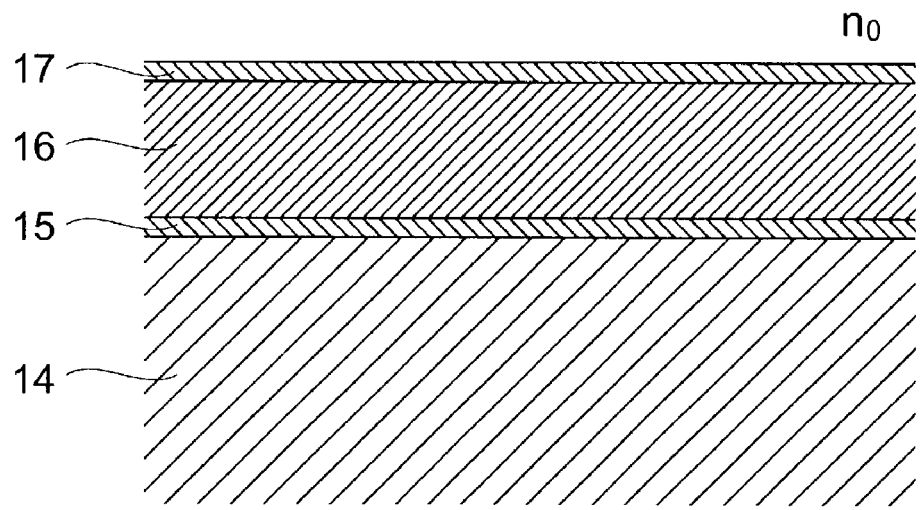
FIGS. 15A and 15B are schematic illustrations of the biochemical sensor of the present invention.
Figure 15B:
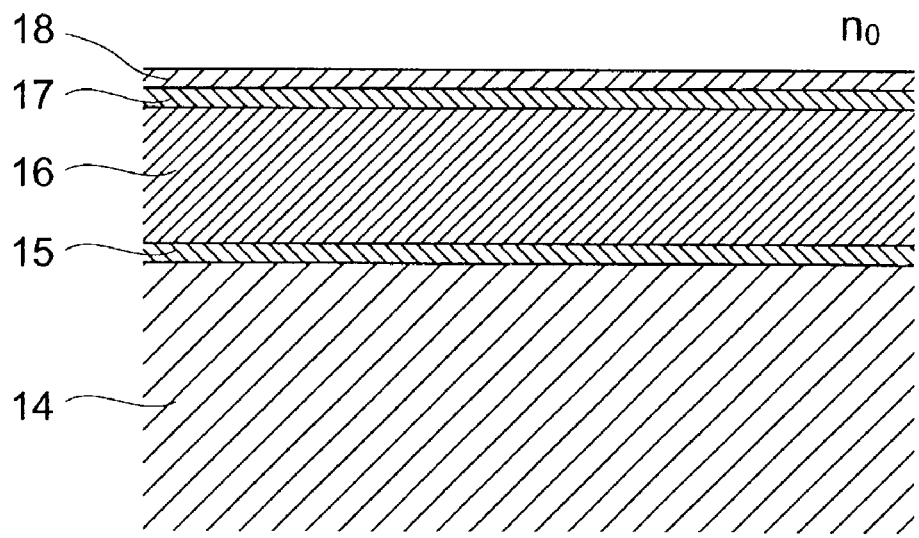
Figure 16:
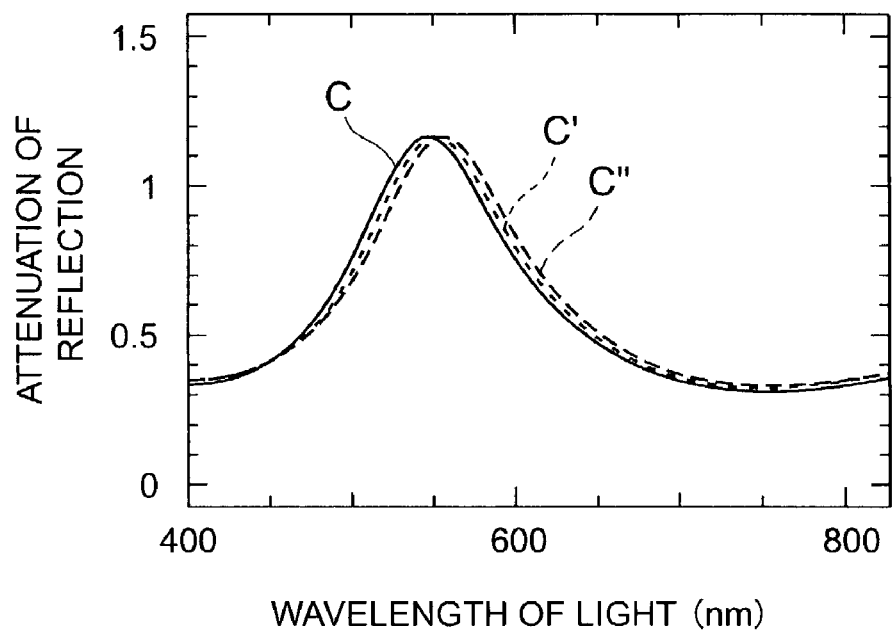
FIG. 16 is a graphic representation of the change of interference color in the present invention.
Figure 17:
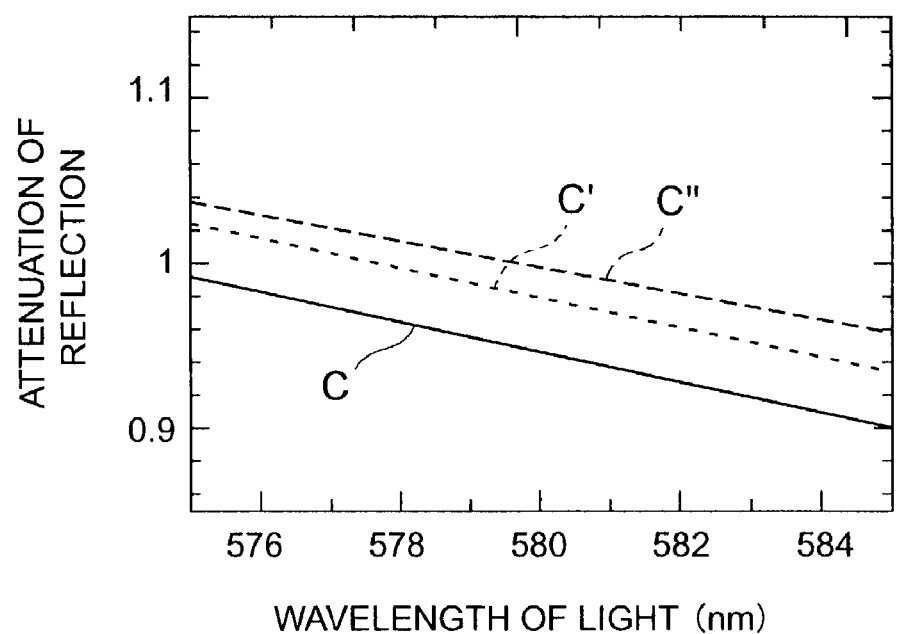
FIG. 17 is also a graphic representation of the change of interference color in the present invention.
Figure 18:
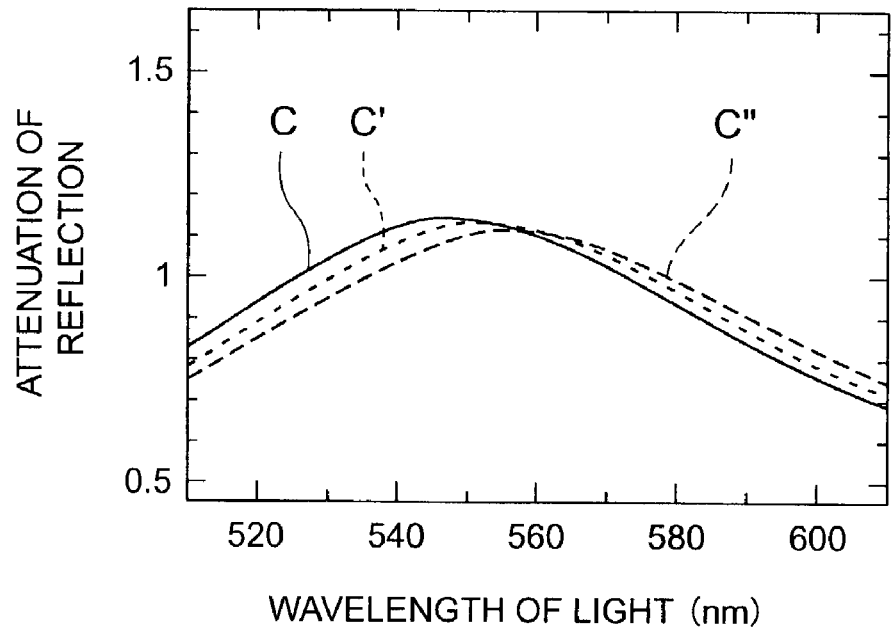
FIG. 18 is another graphic representation of the change of interference color in the present invention.

This sensor displays a distinct interference color in the solution, and this interference color changes on binding of a biochemical substance. FIG. 15 shows a model used for computer simulation. Background refractive index n$_0$ was supposed to be 1.3330. A first biochemical substance (probe) was provided as a layer 17 with a refractive index of 1.5 and a thickness of 10 nm (FIG. 15A). A sample containing a second biochemical substance was supplied to this biochemical sensor to bind the first and second biochemical substances (FIG. 15B). This second biochemical substance is represented as a layer 18 with a refractive index of 1.5 and a thickness of 10 nm. FIGS. 16, 17 and 18 show reflection spectra. Attenuation of reflection on the vertical axis was expressed by $-\log_{10}R$ in the same manner as determination of absorbance, where R is reflectance of the sensor. FIG. 16 shows attenuation of reflection in the wavelength region from 400 nm to 830 nm, FIG. 17 is an enlarged view of the spectra in the wavelength region from 575 nm to 585 nm in FIG. 16, and FIG. 18 is an enlarged view of the spectra in the wavelength region from 510 nm to 610 nm in FIG. 16. In each graph, reflection spectrum of the sensor with no layer of biochemical substance is shown by solid line C, reflection spectrum of the sensor having a layer of a first biochemical substance is shown by dotted line C', and reflection spectrum after binding of a second biochemical substance is shown by broken line C".

It is seen from the reflection spectrum of FIG. 16 that $\lambda_{AR}$ is in the neighborhood of 550 nm. It is also noted that the respective spectra are substantially identical in contour. From FIG. 17 showing the enlarged foot portion of the peak of attenuation of reflection and FIG. 18 showing the spectral portion around $\lambda_{AR}$, the change of reflection spectrum after binding can be confirmed. As seen from the change in FIG. 17, it is possible to detect binding of the second biochemical substance by measuring the change of intensity of reflection of the sensor at a specific wavelength by using a monochromatic light source. On the other hand, it can be learned from FIG. 18 that the position of $\lambda_{AR}$ is shifted to the longer wavelength side on binding of a biochemical substance. A method of determining the amount of shift quantitatively is explained below. First, such amount of shift is approximated by a function staying close to $\lambda_{AR}$ of the reflection spectrum. For this function, there was used the following equation which is represented by the sum of a linear function and a quasi Voigt peak function:

$$f(x) = A + Bx + C\left\{m_u \frac{2}{\pi} \frac{w_2}{4(x-x_c)^2 + w_2^2} + (1-m_u)\sqrt{\frac{4\ln 2}{\pi w_1^2}} \, e^{-4\ln 2\left(\frac{x-x_c}{w_1}\right)^2}\right\}$$

(equation 1)

Figure 19:
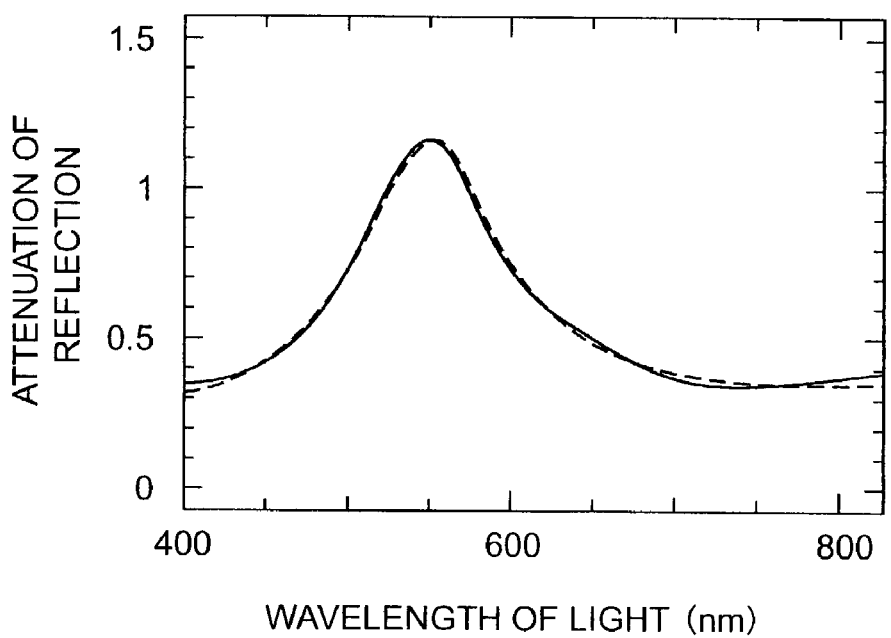
FIG. 19 is a graphic approximation of the reflection spectrum before binding.

Part or all of the constants and factors of A, B, C, $m_u$, $w_1$, $w_2$ and $x_c$ were determined by the least squares method. In FIG. 19, the result of approximation of the reflection spectrum before binding is shown by a broken line. Approximation was made in the wavelength region of 400 nm to 800 nm for all of the constants and factors. It can be seen that the approximation is quite appropriate. The position of $\lambda_{AR}$ is determined by setting it at the center $x_c$ of the quasi Voigt peak function obtained from the above approximation. The position of $\lambda_{AR}$ determined by this method was at 551.21 nm on solid line C, 555.20 nm on dotted line C' and 559.11 nm on broken line C". In this way, it is possible to obtain a change of $\lambda_{AR}$ of 3.91 nm by binding of a second biochemical substance.

EXAMPLE 2

When substrate 14 is made of a material which is light reflective or differs greatly in refractive index from transparent layer 16, it is possible to except reflective layer 15 since reflection of light occurs between substrate 14 and transparent layer 16 without reflective layer 15. Thus, in Example 2, no reflective layer is provided.

An example of the production method of this sensor is described below. On a flat-surfaced glass substrate 14 with a refractive index of 1.5 is vacuum deposited a 120 nm thick transparent layer of titanium oxide (TiO$_x$, refractive index 2.4) 16. Then, as in the preceding example, surface treatment is conducted with 3-aminopropyltrimethoxysilane to introduce an amino group into the surface of transparent layer 16, and a first biochemical substance is fixated to the layer surface in the same way as in Example 1.

Figure 20:
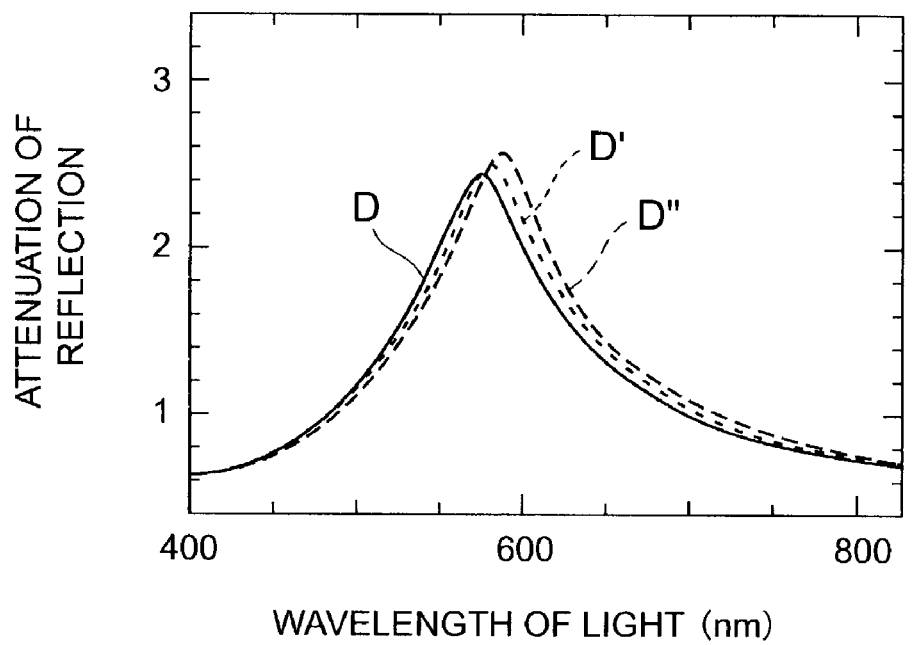
FIG. 20 is a graphic representation of the change of interference color in the present invention.
Figure 21:
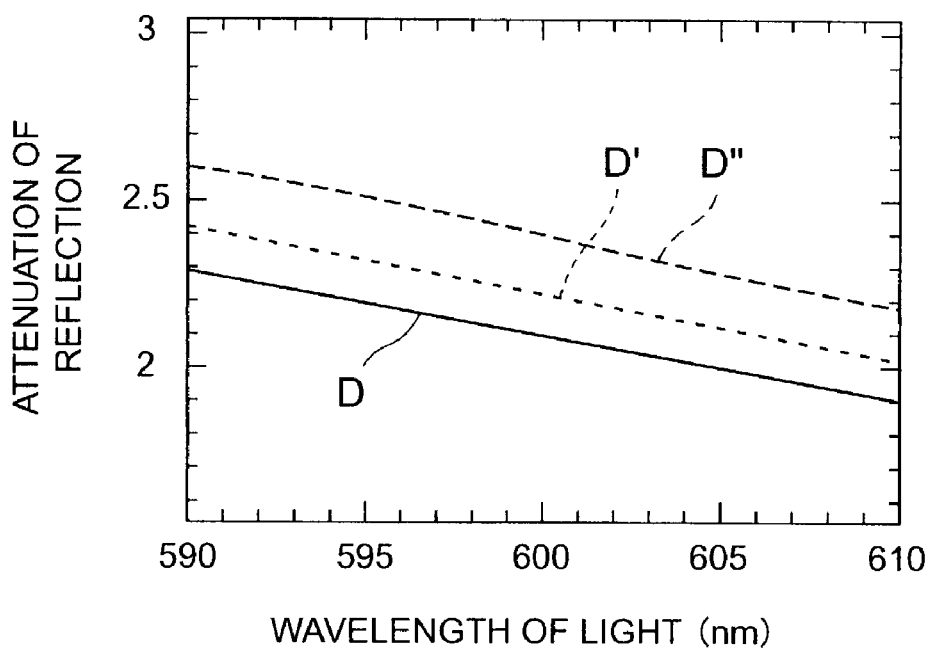
FIG. 21 is also a graphic representation of the change of interference color in the present invention.
Figure 22:
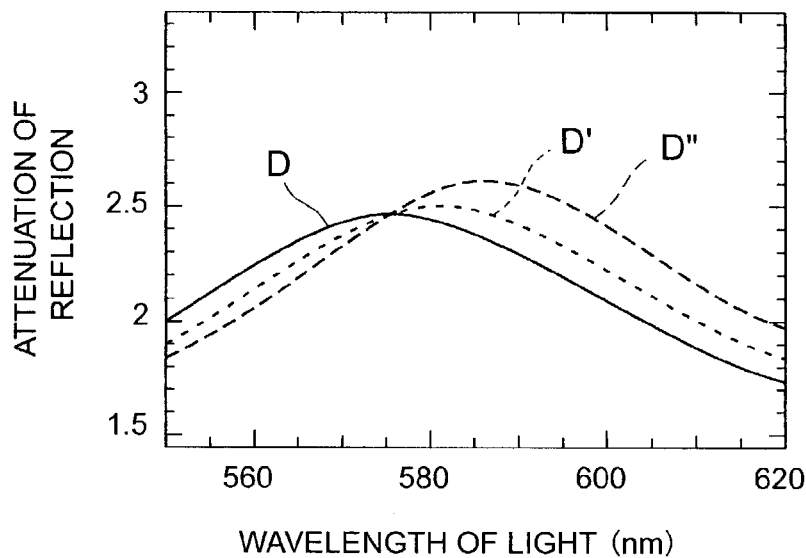
FIG. 22 is another graphic representation of the change of interference color in the present invention.
Figure 23:
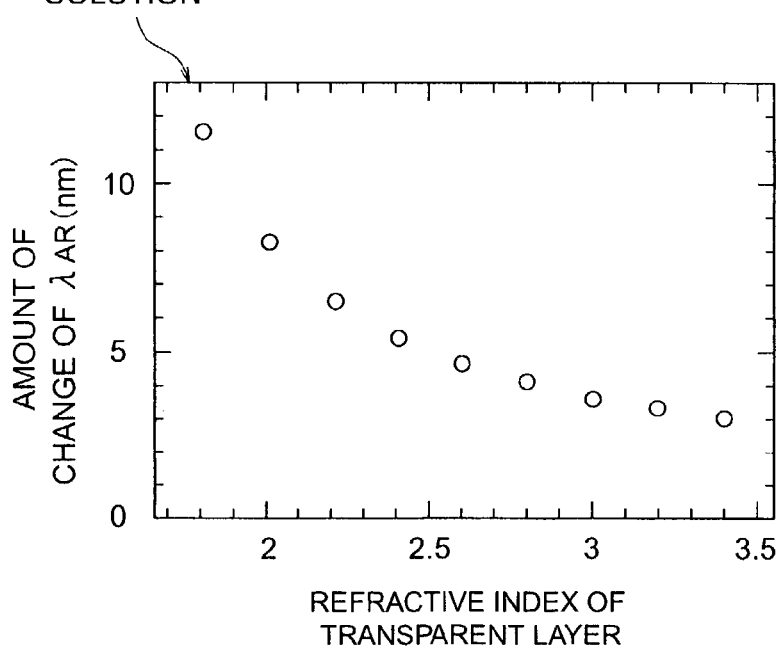
FIG. 23 is a graph showing sensitivity of the biochemical sensor of the present invention.
Figure 24:
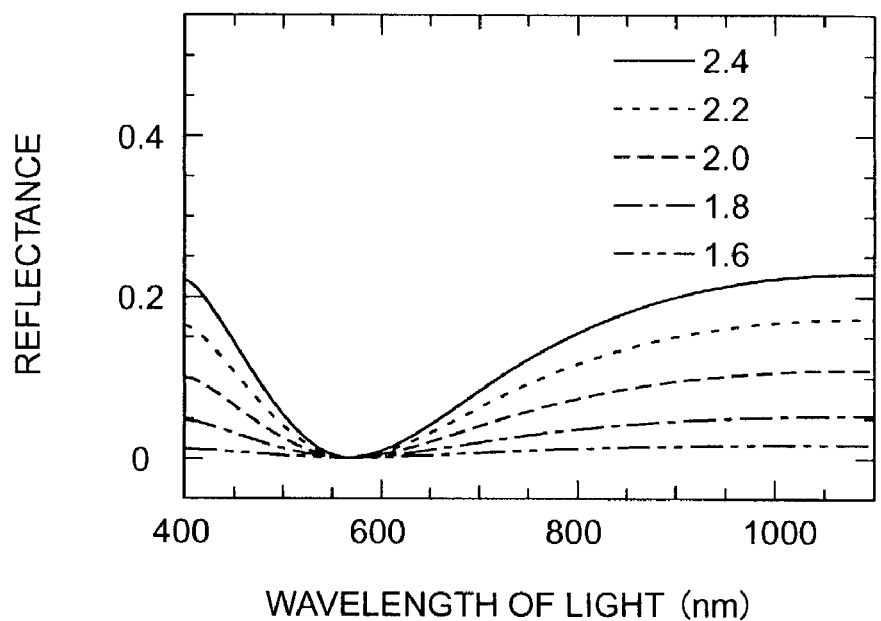
FIG. 24 is a graphic illustration of reflection spectrum of the biochemical sensor of the present invention.

FIGS. 20, 21 and 22 show the reflection spectra and changes thereof in a computer simulation conduced under the same conditions as in the example of FIG. 15, that is, by setting the background refractive index at 1.3330 and setting the refractive index and thickness of the first and second biochemical substance layers at 1.5 and 10 nm, respectively. In each graph, the reflection spectrum with no biochemical substance layer is shown by solid line D, the reflection spectrum of the sensor having a first biochemical substance layer is shown by D', and the reflection spectrum after binding of a second biochemical substance is shown by D". It is seen from the reflection spectrum of FIG. 20 that $\lambda_{AR}$ is in the neighborhood of 580 nm. Also, from FIG. 21 showing the enlarged foot portion of the peak of attenuation of reflection and FIG. 22 showing the portion around $\lambda_{AR}$, the change of reflection spectrum after binding can be confirmed. As is noted from the change in FIG. 21, it is possible to detect binding of a second biochemical substance by measuring the change of reflection intensity of the sensor at a specific wavelength by using a monochromatic light source. On the other hand, it can be seen from FIG. 22 that the position of $\lambda_{AR}$ is shifted to the longer wavelength side on binding of a biochemical substance. The amount of change of $\lambda_{AR}$ by binding of a second biochemical substance which can be determined by conducting the same approximation as in Example 1 in the wavelength region from 470 nm to 800 nm is 5.38 nm, which indicates the substantially same level of detecting sensitivity as the sensor of the preceding example. Also, as a transparent substrate 14 is used, the change of this reflection spectrum can be determined by measuring the reflection spectrum by applying light from the substrate side. For comparison of sensitivity with the cases where the refractive index of transparent layer 16 is not 2.4, dependency of the amount of change of $\lambda_{AR}$ on refractive index of transparent layer 16 is shown in FIG. 23. Here, thickness of transparent layer 16 was selected so that the product of thickness of transparent layer 16 and its refractive index will become constant. As is seen from FIG. 23, the higher the refractive index of transparent layer 16, the smaller the change of $\lambda_{AR}$. In the region where the refractive index of transparent layer 16 is less than 1.8, detection is very difficult because of the small difference in refractive index from the aqueous solution. FIG. 24 shows the results of measurement of the reflection spectra of the sensor in water (refractive index 1.3330) by changing the refractive index of transparent layer 16 in the range from 1.6 to 2.4. Here, too, as in the case of FIG. 23, thickness of transparent layer 16 was selected so that the product of thickness of transparent layer 16 and its refractive index will become constant. Equivalence between each refractive index and reflection spectrum is shown in the graph. It will be seen that reflectance of the sensor lowers with the decrease of refractive index. In the region where refractive index is less than 1.8, detection is very difficult since reflectance of the sensor is confined to only several % or less.

EXAMPLE 3

Illustrated here is an example in which openings are provided in the transparent layer.

FIG. 8 shows an example of sensor chip producing process. A method of producing a sensor is explained with reference to FIG. 8. A 26 mm×20 mm, 0.4 to 0.6 mm thick cover glass for blood cell counter was used as substrate 5. Germanium was vacuum deposited on the glass substrate surface (FIG. 8A) to a thickness of 20 nm to form a reflective layer 6 (FIG. 8B). A low dielectric constant interlayer film material for VLSI, HSG-R7 (Hitachi Chemical Co., Ltd.), was spin coated on the germanium layer to form a transparent layer 7 (FIG. 8C). This transparent layer was approximately 200 nm thick. Natural lithography using silica beads of submicron size was employed for forming submicron openings 10. Monolayer film of silica beads 12 was provided on transparent layer 7 (FIG. 8D). By taking advantage of the difference in etching rate between transparent layer 7 of HSG-R7 and silica beads 12 in reactive ion etching with oxygen gas, transparent layer 7 was subjected to selective anisotropic dry etching in the direction normal to the film to form openings 10 (FIG. 8E). After dry etching, silica beads 12 on the surface were wiped away with ethanol-soaked lens cleaning paper (FIG. 8F). On this surface were vacuum deposited 3 nm thick chromium for adhesion and 20 nm thick gold designed to provide reflective layer 8 (FIG. 8G). In this way, gold is deposited in the inside of openings 10, too, but color is developed by the light interference effect between the reflective layers of gold and germanium with transparent layer 7 interposed therebetween, and as a sensor, there can be obtained substantially the same effect as the structure shown in FIG. 7.

Figure 9:
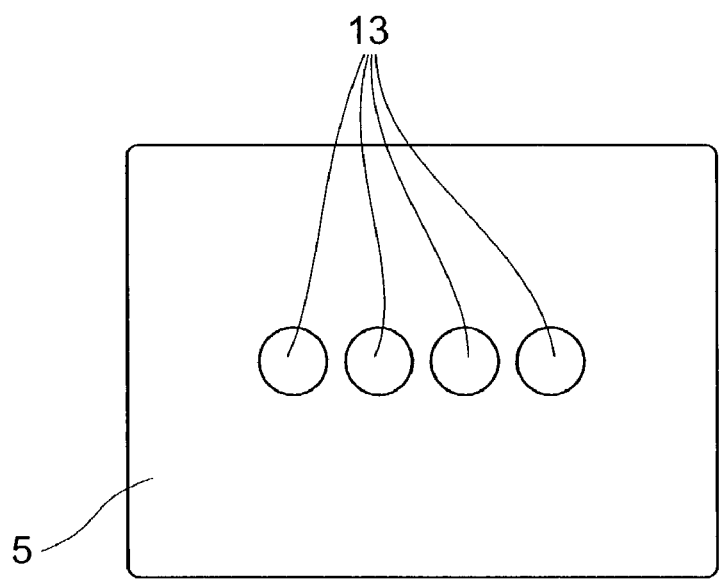
FIG. 9 is a top view of the biochemical sensor of the present invention.

FIG. 9 is a top view of the produced sensor chip. Four sensor sections 13 with a diameter of approximately 3 mm were provided in a row at intervals of 4 mm on substrate 5. These sensor sections 13 developed red color. This is because red light is reflected strongly as $\lambda_{AR}$ of sensor sections 13 is around 530 nm. As an example of fixation of a first biochemical substance to this sensor, the procedure of an antibody fixation process is described below. The above sensor chip was immersed in an ethanol solution of 0.1 mM 11-amino-1-undecanethiol for not less than 10 hours, whereby a self-assembled film of 11-amino-1-undecanethiol was formed on the deposited gold surface and an amino group was introduced to the surface including the inside of openings 10. 2 mg of N-hydroxysuccinimide, 10 mg of water-soluble carbodiimide and 1 mg of an antibody were dissolved in 1 ml of deionized water to activate the carboxyl group in the antibody, and this solution was dropped to the amino group-introduced sensor sections 13 to fixate the antibody to the amino group in the surface by covalent bonding. Thereafter, the sensor chip was rinsed with deionized water and dried by blowing nitrogen gas.

Figure 10:
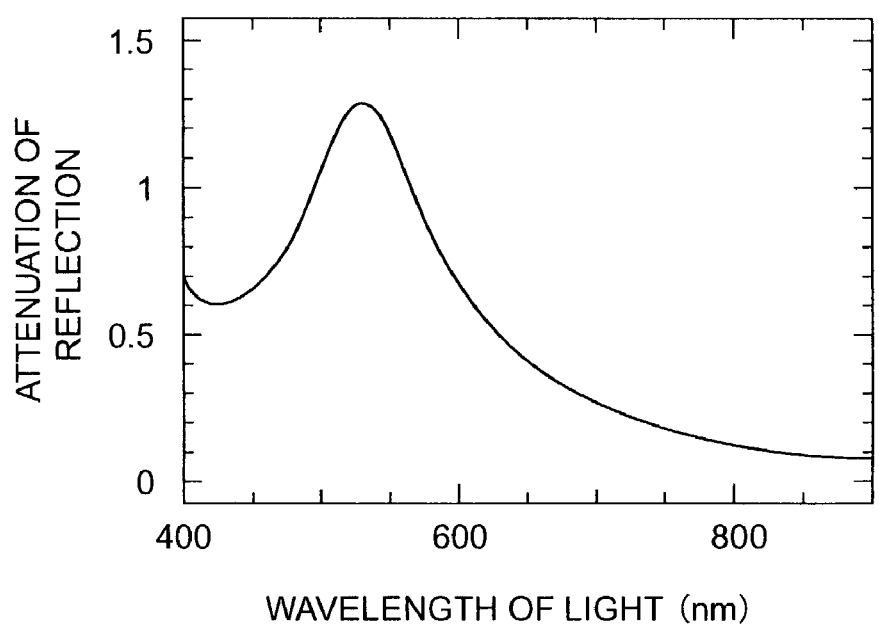
FIG. 10 is a graph showing attenuation of reflection before and after protein binding.
Figure 11:
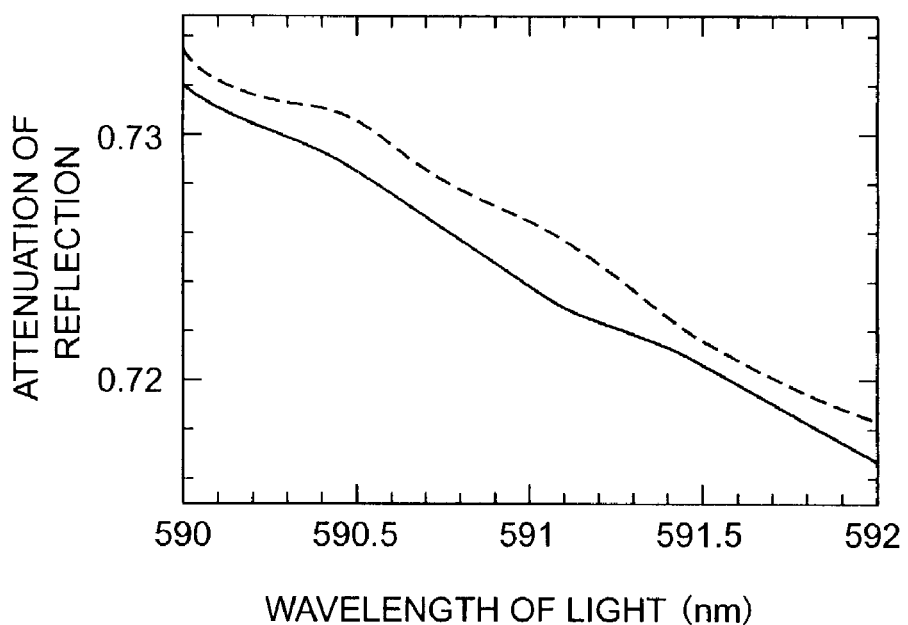
FIG. 11 is also a graph showing attenuation of reflection before and after protein binding.
Figure 12:
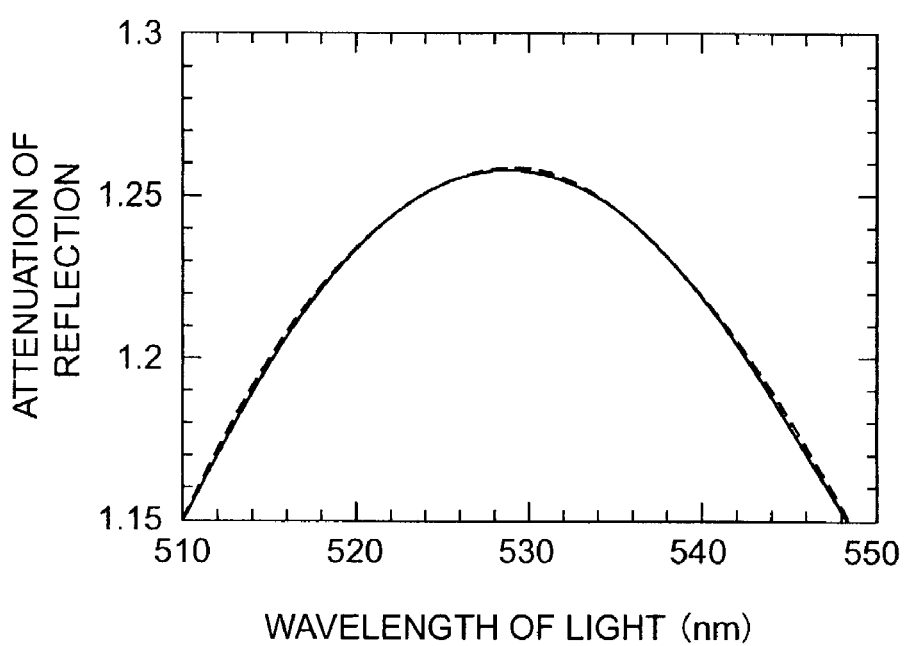
FIG. 12 is another graph showing attenuation of reflection before and after protein binding.

Measurement of the interaction of a protein and an antibody bound to the protein using the sensor chip produced by the above-described process is explained below. Avidin D (produced by Vector Laboratories Inc.) was used as the protein, and Anti-Avidin D (Vector Laboratories) was used as the antibody. The antibody was fixated on the sensor surface by the method described above. A 1 mg/ml (approximately 10 µM) PBS solution of the protein (Avidin D) was used as the sample solution. This sample solution was passed over the sensor surface for about 4 minutes. During this period, binding of the protein and the antibody is saturated. In FIGS. 10, 11 and 12, the reflection spectrum in the PBS buffer solution before protein binding is shown by solid line and the reflection spectrum after protein binding is shown by dotted line. Attenuation of reflection on the vertical axis was expressed by $-\log_{10}(1/1_0)+\alpha$ in the same manner as determination of absorbance. In the above formula, 1 indicates intensity of reflected light from the sensor, $1_0$ indicates intensity of reflection from the standard white board, and $\alpha$ is a constant. FIG. 10 is a graph showing attenuation of reflection at wavelengths from 400 nm to 900 nm, FIG. 11 is a partial enlarged view of FIG. 10 showing attenuation of reflection in the wavelength region from 590 nm to 592 nm, and FIG. 12 is a partial enlarged view of FIG. 10 showing attenuation of reflection in the wavelength region from 510 nm to 550 nm. As is seen from FIG. 10, $\lambda_{AR}$ appeared at around 530 nm. Also, in FIG. 10, the reflection spectra before and after binding overlapped each other, namely they were substantially identical in contour. However, from FIG. 11 showing the foot portion of the peak of attenuation of reflection and FIG. 12 showing its peripheral portion, it is possible to confirm the change of spectrum after binding. As is noted from the change of reflection intensity in FIG. 11, it is possible to detect binding of a second biochemical substance by measuring the change of reflection intensity of the sensor at a specific wavelength by using a monochromatic light source. Non-smoothness of both solid line and dotted line in FIG. 11 is attributable to the fact that the reflection spectra in FIG. 11 were not subjected to smoothening in the wavelength direction for making evaluation for detection using a monochromatic light source.

Change of $\lambda_{AR}$ can be observed from FIG. 12, and here the same approximation as the equation (1) in Example 1 was made for determining such change quantitatively. The result of approximation of the reflection spectrum before binding is shown by broken line in FIG. 13. Approximation was made in the wavelength region from 470 nm to 900 nm. It can be seen that the approximation is quite appropriate. The center of the function obtained from this approximation was expressed as $\lambda_{AR}$. $\lambda_{AR}$ determined by this method was 530.28 nm before binding and 530.35 nm after binding. In this way, binding of proteins and antibodies can be detected from the change of $\lambda_{AR}$.

EXAMPLE 4

Figure 25:
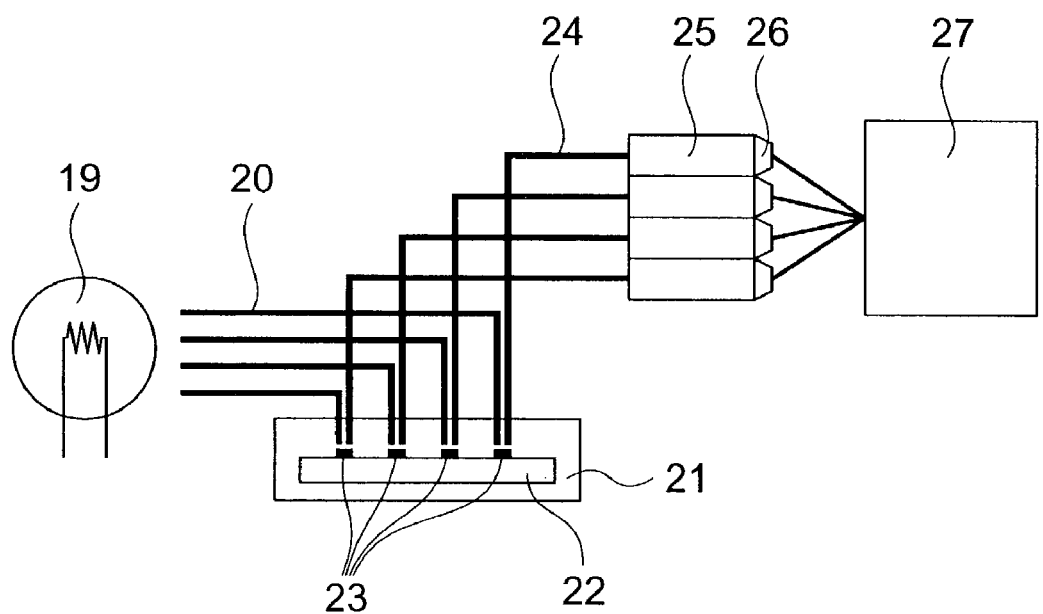
FIG. 25 is a block diagram showing the apparatus of the present invention.
Figure 26:
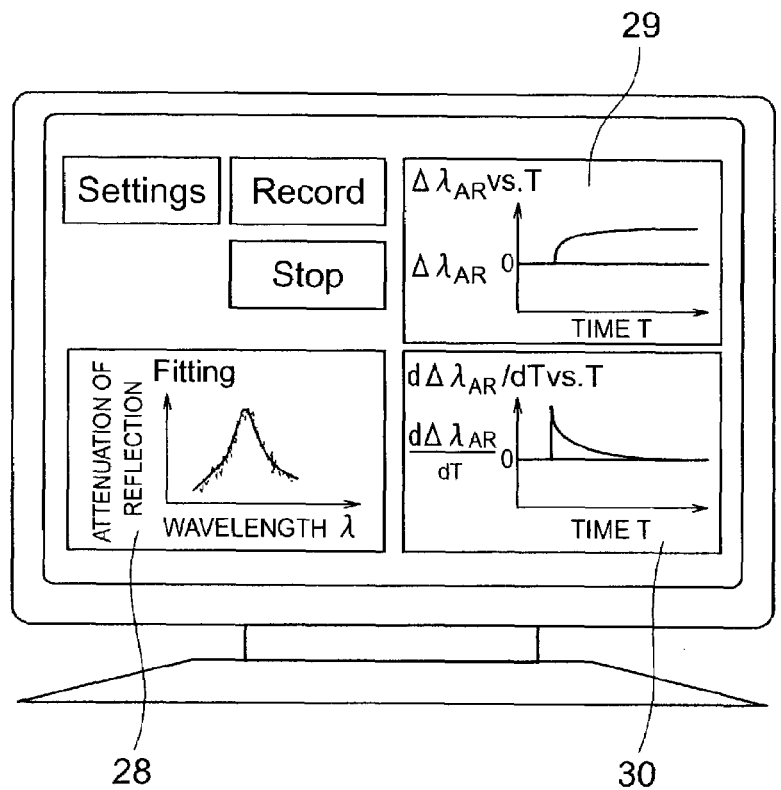
FIG. 26 is a drawing showing the display screen of the calculator in the detection device of the present invention.

A device for making real time detection of the change of interference color of the optical film sensor of the present invention in a solution is explained below with reference to the drawings. FIG. 25 is a block diagram showing an embodiment of the present invention, FIG. 26 is a schematic illustration of an example of computer display in the detecting device of the present invention, FIG. 27 is a perspective view of an example of optical system in the detecting device of the present invention, FIG. 28 is a perspective view of an example of reaction cell in the detecting device of the present invention, FIG. 29 is a sectional view taken along the line E-E' of FIG. 28, and FIG. 30 is a sectional view taken along the line F-F' of FIG. 28.

In the detecting device of the present invention, as illustrated in FIG. 25, light from a white light source 19 such as tungsten lamp is passed through an optical system for irradiation 20 comprising optical fibers and applied to the plural optical film sensor sections 23 described in Examples 1 to 3 on a substrate 22 embedded in a reaction cell 21, and the reflected light from said sensor sections 23 is passed through a collection optical system 24 comprising optical fibers and received and measured instantaneously as reflection spectra by spectrometers 25 and multi-channel photodetectors 26 such as CCD and photodiode array, and the data of the reflection spectra are taken up by computer 27. Computer 27 automatically makes approximation by the least squares method using a function (1) conforming to the reflection attenuation curves of the reflection spectra of optical film sensor sections 23 described in Examples 1 to 3, and the result is displayed like graph 28 in FIG. 26. The wavelength that gives the extremal value of the function obtained from the above approximation, namely $\lambda_{AR}$, is instantly plotted against the time and recorded like graph 29 in FIG. 26. Usually, the measurable interval of wavelength is limited by the interval of pixels of the multi-channel photodetectors such as CCD and photodiode array, but finer determination of $\lambda_{AR}$ is possible by plotting the position of wavelength given as the result of the approximation computation, that is, it is possible to enlarge the dynamic range of measurement of the amount of binding. Also, usually longer spectrometers are required for making finer determination of $\lambda_{AR}$ by using the same multi-channel photodetectors 26. Therefore, as it is possible to obtain the same extent of dynamic range by using the shorter spectrometers than usually employed by the computation of the above approximation, miniaturization of the apparatus is made possible. Further, usually noise produced by multi-channel photodetectors 26 such as CCD and photodiode array is reflected in the reflection spectra, but since such noise is leveled off in the above functional approximation, the S/N ratio is improved and the effective dynamic range is widened. Time differential of graph 29 is displayed and recorded as graph 30. This makes it easier to recognize the inception of binding and saturation.

Figure 27:
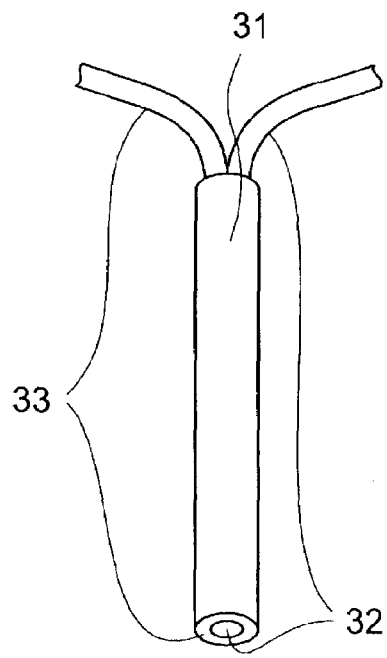
FIG. 27 is a perspective view showing the optical system in the detection device of the present invention.

FIG. 27 shows an embodiment of optical system for irradiation 20 and optical system for collection 24, both using optical fibers. Glass-made optical fibers of 30 microns in diameter are packed in a 2 mm-diameter metal pipe 31. The end of optical fibers 32 opposite from the side occupying the central portion of the optical fiber bundle is located in front of the slit of spectrometer 25, while the end of optical fibers 33 opposite from the side occupying the outside portion of the optical fiber bundle is located in front of while light source 19.

Figure 28:
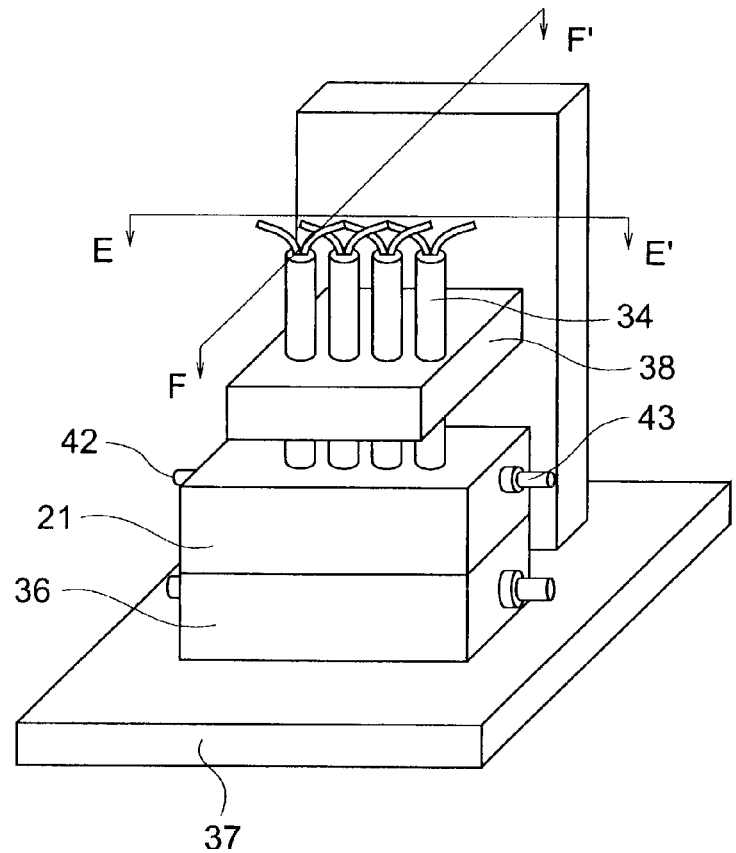
FIG. 28 is a perspective view showing the reaction layer in the detection device of the present invention.
Figure 29:
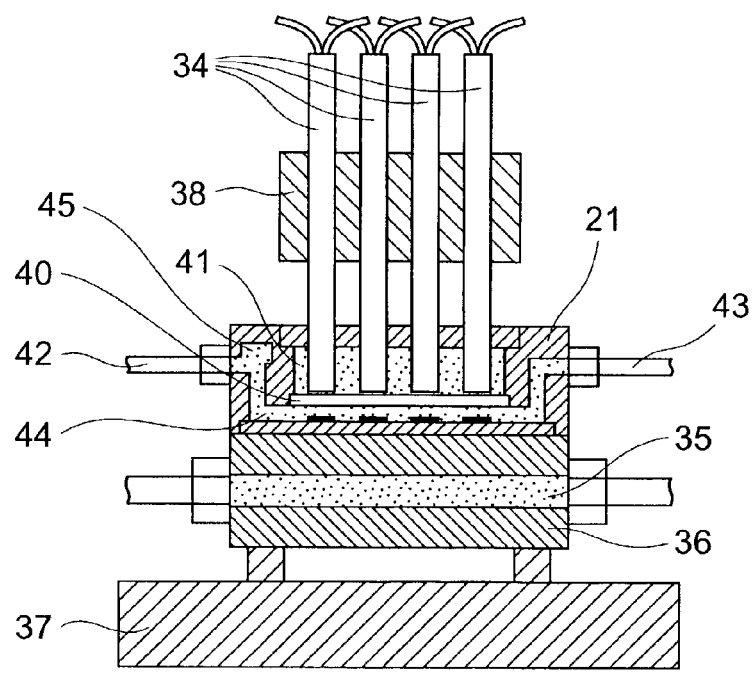
FIG. 29 is a sectional view taken along the line E-E' of FIG. 28.
Figure 30:
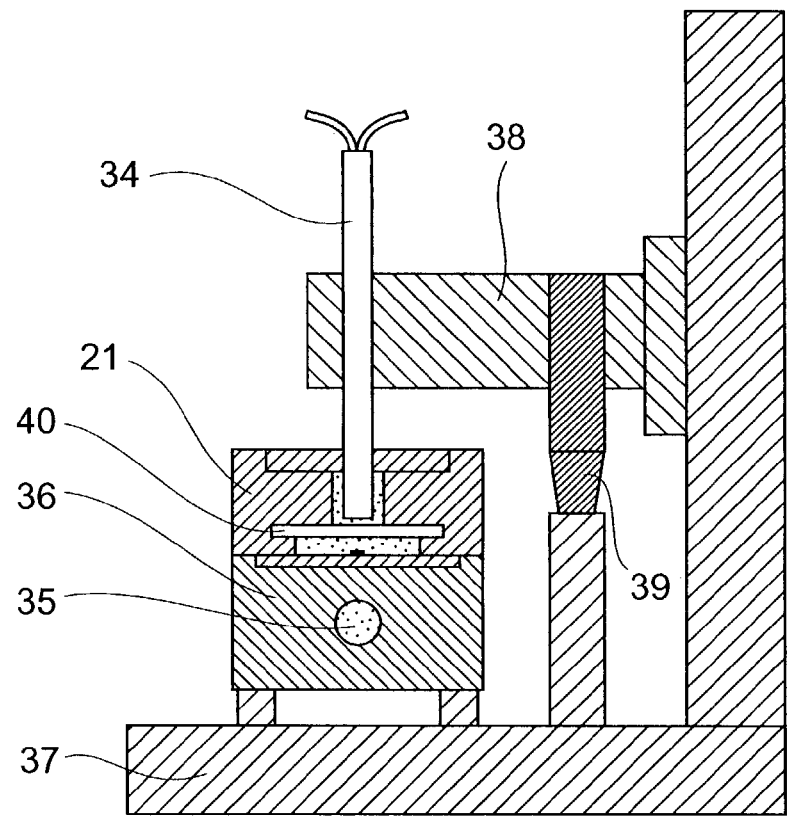
FIG. 30 is a sectional view taken along the line F-F' of FIG. 28.

Referring now to FIGS. 28, 29 and 30, there is shown an example of detecting device using bundle fibers 34 shown in FIG. 27. As shown in FIGS. 28, 29 and 30, bundle fibers 34 are secured to a movable block 38 mounted on a support block 37 having provided thereon a reaction cell 21 and a cooler/heater 36 adapted to control temperature by circulating cooling water or hot water 35, and are positioned immediately above the optical film sensor sections 23. By this arrangement, light is applied from the respective bundle fibers 34 to the corresponding sensor sections 23 immediately therebelow. Stop mechanism 39 is provided to movable block 38 so that the position of bundle fibers 34 relative to the corresponding sensor sections 23 can be reproduced. Generally, interference color of optical films is dependent on the angle of incidence and reflection of the light used for the measurement. With reproduction of the position of bundle fibers 34 by making use of stop mechanism 39, the angle of light applied from optical fibers 33 for optical system 20 and light which is reflected at sensor sections 23 and collected by optical fibers 32 for optical system 24 is reproduced. The angle of light is preferably decided within limits of the irradiating angle and the converging angle of light which are decided by numerical aperture of the optical fibers used. Also, by arranging the condensing optical fibers 32 such that they are surrounded by the irradiating optical fibers 33 as shown in FIG. 27, reproducibility of the obtained reflection spectrum is bettered because in case there is a tilt of disposition of bundle fibers 34 relative to sensor sections 23, its effect is leveled off by such arrangement. The requirement for examining a greater number of types of biochemical substances at one time can be met by increasing the number of optical film sensor sections 23 and bundle fibers 34. Spaces 41 for receiving a liquid are provided between the ends of bundle fibers 34 and window 40 of the reaction cell. These spaces function to reduce reflection of light at the interfaces between the ends of bundle fibers 34 and window 40 of the reaction cell to minimize the undesirable effect on the measurement of the reflection spectra.

Waterdrops or frost may adhere around reaction layer 21 during cooling, but its influence on the measurement of the reflection spectra can be prevented by placing a liquid in spaces 41. Reaction cell 21 was coated in matte black. This makes it possible to prevent scattered light in the reaction cell or light in the chamber from entering the condensing optical system 24. Sample solution 44 containing a biochemical substance is passed through reaction cell 21 by supplying it from inlet 42 and discharging from outlet 43 by using suitable means such as liquid feed pump or sample injector so as to create a situation where said sample solution 44 is allowed to pass through the reaction cell for a certain period of time, thereby conducting real time detection of binding and dissociation of the biochemical substance. Solution inlet 42 and outlet 43 are disposed above the reaction cell and a space 45 for removing air bubbles is provided on the inlet side of the layer. By this arrangement, it is possible to prevent entrance of air bubbles into reaction cell 21 when such air bubbles are present in sample solution 44 containing the biochemical substance to be detected, and to promote discharge of air bubbles when they are generated or enter reaction cell 21. Generally, binding of the biochemical substances has environmental temperature dependency. It is possible to examine temperature dependency of binding of the target biochemical substance by adjusting the temperature of reaction cell 21 by cooler/heater 36. Such cooler/heater 36 may be, for instance, a Peltier element.

Figure 31:
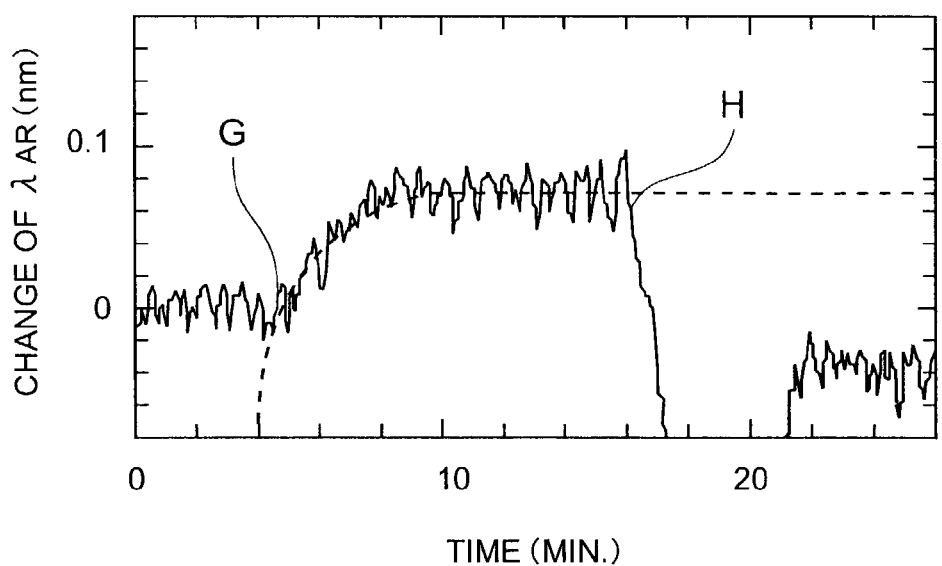
FIG. 31 is a graph showing the result of measurement using the detection device of the present invention.

FIG. 31 shows the result of the real time measurement of the change of $\lambda_{AR}$ using the sensor of Example 3 and the above detecting device. The antibody fixated to the sensor surface, the fixation method and the sample solution are the same as used in Example 3. During the time till reaching G in FIG. 31, a PBS buffer solution is supplied to the sensor surface. $\lambda_{AR}$ during supply of this PBS buffer solution was 530.30 nm. The vertical axis represents the amount of change of $\lambda_{AR}$ from 530.30 nm. From the point of time indicated by G in FIG. 31, the PBS solution of Avidin D is flown over the sensor to initiate binding, causing rise of $\lambda_{AR}$ in conformity to the exponential function shown by the broken line. Thereby saturation of the amount of binding was confirmed. When 10 mM hydrochloric acid was supplied to dissociate binding at the point H, $\lambda_{AR}$ returned to the original value after dissociation. The time required for the measurement of binding and dissociation was about 20 minutes. The small amount of change, 0.07 nm, of $\lambda_{AR}$ by protein binding is probably because the amount of bound Avidin D fell short of providing enough density to form a single-layer film.

The above method for real time detection of reflected light can be applied either when using an optical film of a large refractive index without openings as in Examples 1 and 2 or when using an optical film having openings as in Example 3.

In the instant embodiment where real time detection of reaction is possible, measurement of binding of biochemical substances can be made at a higher throughput.

With the above-described concept of the present invention, it is possible to make measurement of binding of biochemical substances at a high throughput and with high precision.

It should be further understood by those skilled in the art that although the foregoing description has been made on embodiments of the invention, the invention is not limited thereto and various changes and modifications may be made without departing from the spirit of the invention and the scope of the appended claims.

What is claimed is:

1. A method of detecting biochemical substances which comprises the steps of:
   preparing a substrate, an optical film having a refractive index of 1.8 or more formed on said substrate, and a sensor chip comprising a first biochemical substance formed on said optical film;
   supplying to said sensor chip an aqueous solution containing a second biochemical substance which is bound with said first biochemical substance;
   irradiating said sensor chip with light with an optical fiber;
   detecting the reflected light from said sensor chip with said optical fiber while it is in a pre-dried state; and
   determining a wavelength that provides minimal reflectance, wherein the minimal reflectance of the wavelength is due to attenuation of reflection by an interference effect of said optical film, and
   wherein said optical fiber is secured to a movable block provided with a stop mechanism, and said stop mechanism is configured to reproducibly position said optical fiber relative to said optical film, and
   wherein a window is provided between said optical fiber and said sensor chip, and a liquid is provided between said optical fiber and said window.

2. The method according to claim 1 wherein a reflective layer is provided between said substrate and said optical film.

3. The method according to claim 1 wherein the thickness of said optical film is not less than 10 nm and not more than 10 μm.

4. The method according to claim 1 wherein said optical film has a refractive index of not greater than 3.

* * * * *